(12) United States Patent
Loesel et al.

(10) Patent No.: US 8,807,752 B2
(45) Date of Patent: Aug. 19, 2014

(54) SYSTEM AND METHOD WITH REFRACTIVE CORRECTIONS FOR CONTROLLED PLACEMENT OF A LASER BEAM'S FOCAL POINT

(75) Inventors: Frieder Loesel, Mannheim (DE); Kristian Hohla, Munich (DE); Gwillem Mosedale, Munich (DE)

(73) Assignee: Technolas Perfect Vision GmbH, Munich (DE)

( * ) Notice: Subject to any disclaimer, the term of this patent is extended or adjusted under 35 U.S.C. 154(b) by 0 days.

(21) Appl. No.: 13/415,679

(22) Filed: Mar. 8, 2012

(65) Prior Publication Data

US 2013/0235341 A1   Sep. 12, 2013

(51) Int. Cl.
   *A61B 3/14*   (2006.01)
(52) U.S. Cl.
   USPC .............................................. 351/208; 606/4
(58) Field of Classification Search
   USPC ........... 351/206–208, 246; 606/4, 5, 107, 166
   See application file for complete search history.

(56) References Cited

U.S. PATENT DOCUMENTS

| | | | |
|---|---|---|---|
| 4,452,506 A | 6/1984 | Reeve et al. | |
| 4,474,423 A | 10/1984 | Bisbee et al. | |
| 4,538,608 A | 9/1985 | L'Esperance, Jr. | |
| 4,665,913 A | 5/1987 | L'Esperance, Jr. | |
| 4,812,641 A | 3/1989 | Ortiz, Jr. | |
| 4,838,631 A | 6/1989 | Chande et al. | |
| 4,846,172 A | 7/1989 | Berlin | |
| 4,907,586 A | 3/1990 | Bille et al. | |
| 5,098,426 A | 3/1992 | Sklar | |
| 5,159,361 A | 10/1992 | Cambier et al. | |
| 5,281,211 A | 1/1994 | Parel et al. | |
| 5,336,217 A | 8/1994 | Buys et al. | |
| 5,493,109 A | 2/1996 | Wei et al. | |
| 5,549,632 A | 8/1996 | Lai | |
| 5,620,436 A | 4/1997 | Lang et al. | |

(Continued)

FOREIGN PATENT DOCUMENTS

| | | |
|---|---|---|
| EP | 1364632 A1 | 11/2003 |
| EP | 1769732 A2 | 4/2007 |

(Continued)

OTHER PUBLICATIONS

Sacks et al., High Precision Subsurface Photodisruption in Human Sclera, Journal of Biomedical Optics, Jul. 2002, pp. 442-450, vol. 7, No. 3.

(Continued)

*Primary Examiner* — Darryl J Collins
*Assistant Examiner* — Gary O'Neill
(74) *Attorney, Agent, or Firm* — Nydegger & Associates

(57) ABSTRACT

A methodology is provided for correcting the placement of a laser beam's focal point. Specifically, this correction is done to compensate for displacements of the focal point that may be caused when implant material (e.g. an Intraocular Lens (IOL)) is positioned on the optical path of the laser beam. The methodology of the present invention then determines a deviation of the laser beam's refracted target position (uncompensated) from its intended target position. A calculation of the deviation includes considerations of the laser beam's wavelength and refractive/diffractive characteristics introduced by the implant material. This deviation is then added to the refracted target position to make the refracted target position coincide with the intended target position of the focal point. The laser beam will then focus to its intended target position.

19 Claims, 1 Drawing Sheet

(56) References Cited

U.S. PATENT DOCUMENTS

| | | |
|---|---|---|
| 5,720,894 A | 2/1998 | Neev et al. |
| 5,728,156 A * | 3/1998 | Gupta et al. ............... 623/6.26 |
| 5,865,832 A | 2/1999 | Knopp et al. |
| 6,004,314 A | 12/1999 | Wei et al. |
| 6,010,497 A | 1/2000 | Tang et al. |
| 6,059,772 A | 5/2000 | Hsia et al. |
| 6,091,074 A | 7/2000 | Korevaar |
| 6,097,522 A | 8/2000 | Maerki et al. |
| 6,099,522 A | 8/2000 | Knopp et al. |
| 6,322,556 B1 | 11/2001 | Gwon et al. |
| 6,454,761 B1 | 9/2002 | Freedman |
| 6,485,413 B1 | 11/2002 | Boppart et al. |
| 6,514,241 B1 | 2/2003 | Hsia et al. |
| 6,702,809 B1 | 3/2004 | Knopp et al. |
| 6,726,680 B1 | 4/2004 | Knopp et al. |
| 6,751,033 B2 | 6/2004 | Goldstein et al. |
| 6,787,733 B2 | 9/2004 | Lubatschowski et al. |
| 6,913,603 B2 | 7/2005 | Knopp et al. |
| 6,966,905 B2 | 11/2005 | Bille |
| RE40,420 E | 7/2008 | Dick et al. |
| 7,655,002 B2 | 2/2010 | Myers |
| 8,088,124 B2 | 1/2012 | Loesel et al. |
| 2002/0173778 A1 | 11/2002 | Knopp et al. |
| 2003/0074150 A1 | 4/2003 | Goldstein et al. |
| 2004/0021874 A1 | 2/2004 | Shimmick |
| 2004/0059321 A1 | 3/2004 | Knopp et al. |
| 2004/0199149 A1 | 10/2004 | Myers et al. |
| 2005/0024586 A1 | 2/2005 | Teiwes et al. |
| 2005/0165387 A1 | 7/2005 | Lubatschowski et al. |
| 2006/0192921 A1 | 8/2006 | Loesel et al. |
| 2006/0200113 A1 | 9/2006 | Haffner et al. |
| 2007/0027438 A1 | 2/2007 | Loesel |
| 2007/0129775 A1 | 6/2007 | Mordaunt et al. |
| 2007/0173794 A1 | 7/2007 | Frey et al. |
| 2008/0177256 A1 | 7/2008 | Loesel et al. |
| 2009/0005764 A1 | 1/2009 | Knox et al. |
| 2009/0131921 A1 | 5/2009 | Kurtz et al. |
| 2009/0149840 A1 | 6/2009 | Kurtz |
| 2010/0004641 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0082017 A1 * | 4/2010 | Zickler et al. ............... 606/4 |
| 2010/0106143 A1 | 4/2010 | Riedel et al. |
| 2010/0137850 A1 | 6/2010 | Culbertson et al. |
| 2010/0324542 A1 | 12/2010 | Kurtz |
| 2010/0324543 A1 | 12/2010 | Kurtz |
| 2011/0184392 A1 | 7/2011 | Culbertson et al. |
| 2011/0184395 A1 | 7/2011 | Schuele et al. |
| 2011/0202044 A1 | 8/2011 | Goldshleger et al. |
| 2011/0202046 A1 | 8/2011 | Angeley et al. |
| 2011/0251601 A1 * | 10/2011 | Bissmann et al. ............... 606/5 |
| 2011/0319875 A1 | 12/2011 | Loesel |
| 2012/0016352 A1 * | 1/2012 | Dick et al. ............... 606/5 |

FOREIGN PATENT DOCUMENTS

| | | |
|---|---|---|
| EP | 2301423 A1 | 3/2011 |
| WO | 0189373 A3 | 11/2001 |
| WO | 2007084694 A2 | 7/2007 |
| WO | 2009033111 A2 | 3/2009 |
| WO | 2009059251 A2 | 5/2009 |
| WO | 2013017513 A2 | 2/2013 |

OTHER PUBLICATIONS

Chai et al., Aqueous Humor Outflow Effects of Partial Thickness Channel Created by a Femtosecond Laser in Ex Vivo Human Eyes, Optical Interactions with Tissue and Cells XVIII, 2007, pp. 1-8, Proc of SPIE, vol. 6435.

PCT International Search Report; Application No. PCT/IB2013/000512; Mar. 5, 2013.

* cited by examiner

SYSTEM AND METHOD WITH REFRACTIVE CORRECTIONS FOR CONTROLLED PLACEMENT OF A LASER BEAM'S FOCAL POINT

FIELD OF THE INVENTION

The present invention pertains generally to methodologies for the guidance and control of laser beam focal points. More particularly, the present invention pertains to methods for placing laser beam focal points, with increased accuracy, to within tolerances of only several microns. The present invention is particularly, but not exclusively, useful for methodologies that correct the displacement of a laser beam's focal point when holographic, accommodating or refractive/diffractive materials are positioned on the laser beam's optical path.

BACKGROUND OF THE INVENTION

Optical Coherence Tomography (OCT) incorporates well known optical techniques for creating images of objects in various environments. Of particular interest here are images of different anatomical structures inside an eye. For example, insofar as ophthalmic laser procedures are concerned, OCT has been effectively used for establishing the structural relationships that anatomically exist between optical elements inside the eye, such as the cornea, the anterior chamber, the crystalline lens, the vitreous and the retina. In this context, OCT has been particularly effective when used to establish a reference datum in the eye that can be used for the guidance and control of a laser focal point during ophthalmic surgery. It will be appreciated by the skilled artisan that imaging techniques other than OCT may be used where appropriate. For example, techniques such as Scheimpflug imaging, confocal imaging, optical range finding, two-photon imaging or acoustical (non-optical) imaging may be useful.

As will be readily appreciated, in an ophthalmic surgical procedure, precision and accuracy in the placement and movement of a laser beam's focal point are of utmost importance. In particular, this precision and accuracy are important in situations (procedures) wherein the placement of a laser beam's focal point must be accurate to within tolerances as small as plus or minus five microns ($\pm 5$ μm). The situation can be complicated, however, when optical materials (e.g. an Intraocular Lens (IOL) or inlays such as corneal inlays) are implanted into the eye, and are located on the optical path of the laser beam. In such a situation, the holographic, accommodating or refractive/diffractive changes that are introduced into the optical path by the implant material may have an untracked effect on the placement of the focal point. Stated differently, an intended focal point location (as might be established using imaging techniques) may be changed by the implant material such that the actual focal point location is not as intended. Such a deviation in focal point location is particularly problematic when very small tolerances are required for focal point placement, and the deviation is also very small.

By way of example, consider the situation presented by Posterior Capsule Opacity (PCO). The problem presented by PCO after a cataract surgery is that biological growths will sometimes intrude into the space between the posterior surface of an IOL and the posterior capsule. A consequence here is that the patient's vision deteriorates and becomes hazy. To correct this, it is envisioned that lasers can be used to ablate or remove these biological growths. It happens that the space where these biological growths are located, i.e. in the optical zone between the posterior surface of an IOL and the posterior capsule, is very small. Moreover, it is important that the IOL not be damaged during the removal of the offending biological growth.

In light of the above, it is an object of the present invention to provide a method for correcting the placement of a laser beam's focal point to compensate for displacements of the focal point caused by implant material positioned on an optical path of the laser beam. Another object of the present invention is to provide a method for augmenting OCT or other imaging capabilities for use in the guidance and control of a laser beam's focal point. Still another object of the present invention is to provide a methodology for treating ophthalmic conditions behind implant material deep in an eye (e.g. crystalline lens, vitreous or retina) which is simple to implement, is easy to use and is comparatively cost effective.

SUMMARY OF THE INVENTION

In accordance with the present invention, a method is provided for correcting the placement of a laser beam's focal point. Specifically, this correction is done to compensate for displacements of the focal point that may be caused when implant material (e.g. an Intraocular Lens (IOL) or a (corneal) inlay or a temporary intraocular material (e.g. a viscoelastic)) is positioned on the optical path of the laser beam. In overview, the methodology of the present invention determines a deviation of the laser beam's refracted focal point (target position) from its intended target position.

As a first step in the methodology of the present invention, an intended target position is identified for the focal point of the laser beam. Preferably, this identification is accomplished relative to a reference datum, using Optical Coherence Tomography (OCT) techniques or other imaging techniques, such as Scheimpflug imaging, confocal imaging, optical range finding, two-photon imaging or acoustical (non-optical) imaging. As envisioned for the present invention the reference datum will most likely be a convenient algorithm which is compatible with the procedure that is being performed. In the event, once a reference datum has been established, and an intended target position has been identified, the effect of implant material is determined.

It is an important aspect of the present invention that a volume of implant material be accurately defined. In particular, the definition of the implant material will include considerations of the dimensional measurements of the volume, the refractive index of the implant material, and an overall configuration of the volume of material. Additionally, the wavelength ($\lambda$) of the laser beam is considered. The defined volume of implant material is then analytically oriented on the optical path, and a refracted target position is calculated. Importantly, this refracted target position will account for the refractive/diffractive optical characteristics that are introduced by the implant material. Next, the refracted target position is compared with the intended target position and a deviation between the two positions is measured. For the present invention, this deviation will be three dimensional ($\Delta_{xyz}$), and it will have separately identifiable x, y and z components.

In an operation of the present invention, the laser beam is focused along the optical path to its focal point. At this point, however, the deviation ($\Delta_{xyz}$) will have already been added to the refracted target position. Consequently, with this addition, the deviation compensates for the implant material by correcting the refracted target position of the focal point so that it will be coincident with the intended target position.

In addition to the above considerations for correcting the placement of a laser beam's focal point, there are also other considerations that go to the efficacy of the focal point. Specifically, aside from concerns for focal point displacement, the quality of the focal point can also be adversely affected by implant material. With this in mind, additional considerations involving the implant material include: refractive effects that defocus the laser beam; diffractive effects that disperse energy into higher diffraction orders; and reflective effects that will also disperse energy in the beam. Collectively, the refractive/diffractive/reflective (r/d/r) effects will degrade the fluence (energy/unit area) of the beam. The present invention recognizes that in some instances it may be advantageous to compensate for the r/d/r effects with an appropriate adjustment in laser pulse energy.

As noted above, the deviation ($\Delta_{xyz}$) provides for a three dimensional compensation. In the specific context of PCO, this allows its component along the optical path (i.e. $\Delta_z$) to be used for maintaining the intended target position of the focal point beyond a predetermined distance "d" from the volume of implant material. An objective here, in the case of an IOL, is that the implant material will not be damaged by the laser beam.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
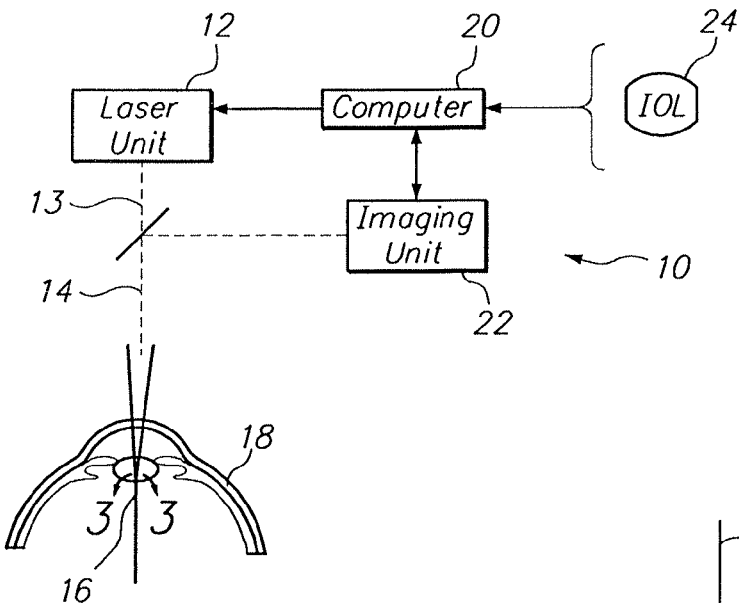
FIG. 1 is a schematic presentation of the system components that are employed for an operation of the present invention.

Referring initially to FIG. 1 a system for implementing the methodologies of the present invention is shown and is generally designated 10. As shown, the system 10 includes a laser unit 12 for generating a laser beam 13 that will be directed along an optical path 14, and focused to a focal point 16. For the present invention, it is intended the focal point 16 be located in an eye 18, in a manner disclosed below. Preferably, the laser unit 12 will generate a pulsed laser beam 13 having ultra-short pulses (e.g. less than one nanosecond duration) and the laser beam 13 will have a wavelength ($\lambda$) that is suitable for ablating tissue in the eye 18 with Laser Induced Optical Breakdown (LIOB), or removing such tissue by employing a laser-acoustic-mechanical effect on tissue.

FIG. 1 also shows that the system 10 includes a computer 20 which is connected with the laser unit 12 to guide and control the laser unit 12. Also, the computer 20 is connected to an imaging unit 22 for using images from the imaging unit 22 for guidance and control, as well as analytical purposes. For purposes of the present invention, the imaging unit 22 is preferably of a type that is capable of creating three dimensional images of tissues inside the eye 18 using Optical Coherence Tomography (OCT) techniques.

Still referring to FIG. 1, it is to be appreciated that an important input to the computer 20 is the definition of an implant material, such as the Intraocular Lens (IOL) 24. In particular, the present invention envisions that the implant material (e.g. IOL 24) will be positioned on the optical path 14 during an operation of the system 10. In this case, it is well known that the refractive/diffractive properties of the IOL 24 will alter the optical path 14.

In the context of an ophthalmic laser surgical procedure, any optical alteration of the optical path 14 by an IOL 24 needs to be accounted for. Accordingly, the definition of a volume of implant material (e.g. IOL 24) must be precise and accurate. Importantly, such a definition must include considerations of the dimensional measurements of the volume of the IOL 24, the refractive index of the material that is used to make the IOL 24, and its overall configuration. Further, consideration should also be given to the wavelength ($\lambda$) of the laser beam 13 that will be used for the selected ophthalmic laser surgical procedure. The consequences of all of this will be best appreciated with reference to FIG. 2.

Figure 2:
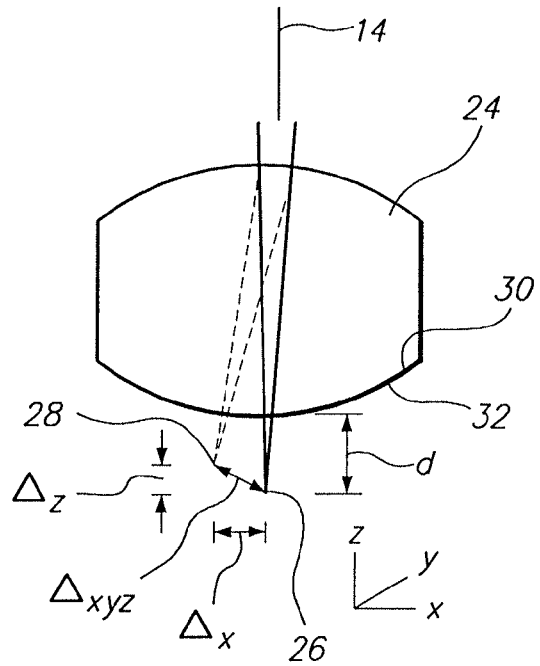
FIG. 2 is an illustration of a deviation as calculated for the methodology of the present invention.

By way of example, in FIG. 2 it is expected that, in accordance with a particular ophthalmic laser surgical procedure (e.g. Posterior Capsule Opacity (PCO)), the focal point 16 of the laser beam 13 on optical path 14 will be located at an intended target position 26. In this example however, based on the optical definition of the IOL 24, and the following calculations made by the computer 20, it is determined that due to the influence of IOL 24, the focal point 16 is actually at the refracted target position 28. The consequence here is a deviation $\Delta_{xyz}$ in the location of the focal point 16. As indicated in FIG. 2, the deviation $\Delta_{xyz}$ is three dimensional and will have x ($\Delta_x$), y ($\Delta_y$) and z ($\Delta_z$) components.

In an operation of the system 10, an intended target position 26 is first identified relative to a reference datum 30 (e.g. posterior surface 32 of IOL 24). The definition of IOL 24 that has been previously given as input to the computer 20 is then considered. Using the optical definition of IOL 24, the computer 20 calculates a refracted target position 28 on the optical path 14. By comparing the refracted target position 28 with the intended target position 26, a resultant deviation $\Delta_{xyz}$, which is the location difference between the intended target position 26 and the refracted target position 28, is also calculated. Specifically, the deviation $\Delta_{xyz}$ is indicative of the optical effect that IOL 24 has had on the optical path 14. The computer 20 then adds the deviation $\Delta_{xyz}$ to the refracted target position 28, to thereby make the focal point 16 coincident with the intended target position 26.

Once the above corrections for the focal point 16 have been appropriately calculated by the computer 20, and have been entered for all programmed movements of the focal point 16, an ophthalmic procedure can be performed. In particular, consider a PCO procedure.

Figure 3:
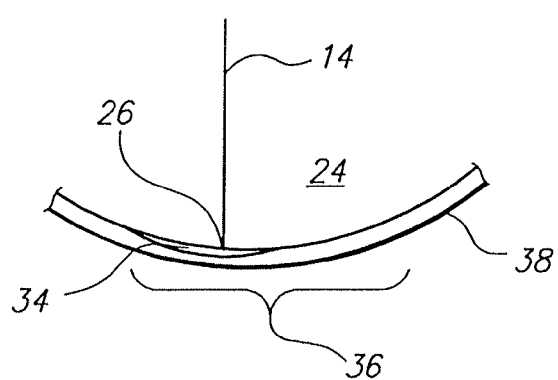
FIG. 3 is a cross section view of the posterior capsule of an eye as seen along the line 3-3 in FIG. 1.

In FIG. 3, a PCO procedure is shown being performed wherein the optical path 14 of the laser unit 12 is controlled and guided by the computer 20 to ablate biological growth 34. Specifically, in this case, the tissue to be ablated is the biological growth 34 that has intruded into the optical zone 36 of the IOL 24, between the IOL 24 and the posterior capsule 38. Importantly, with compensation provided by the deviation $\Delta_{xyz}$, the intended target position 26 that is now coincident with the focal point 16 on optical path 14, can be maintained with improved accuracy within the biological growth 34. Moreover, the component of the deviation $\Delta_{xyz}$ that lies along the optical path 14 (i.e. $\Delta_z$) can be appropriately adjusted as required to maintain the intended target position 26 (i.e. focal point 16) beyond a predetermined distance "d" from the posterior surface 32 of IOL 24. Accordingly, damage to the IOL 24 can be avoided.

While the particular System and Method for Controlled Reduction of Opacities in an Eye as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for correcting the placement of a laser beam's focal point outside an implant material to compensate for displacements of the focal point caused when the implant material becomes positioned on an optical path of the laser beam, the method comprising the steps of:
    identifying an intended target position for the focal point of the laser beam, wherein the intended target position is outside the implant material and is identified relative to a reference datum;
    defining a volume of the implant material to include dimensional measurements of the volume, a refractive index of the implant material, and a configuration of the volume;
    orienting the optical path of the laser beam relative to the defined volume of implant material;
    calculating a refracted target position based on the orienting step, said refracted target position accounting for refractive optical characteristics introduced by the implant material;
    measuring a deviation between the intended target position and the refracted target position;
    focusing the laser beam along the optical path to the focal point; and
    correcting the focusing step to compensate for the deviation measured in the measuring step by making the refracted target position of the focal point substantially coincident with the intended target position.

2. A method as recited in claim 1 wherein the reference datum is selected from a group comprising Optical Coherence Tomography (OCT), Scheimpflug imaging, confocal imaging, optical range finding, two-photon imaging or acoustical (non-optical) imaging techniques.

3. A method as recited in claim 1 wherein the reference datum is an algorithm.

4. A method as recited in claim 1 wherein the deviation ($\Delta_{xyz}$) provides for a three dimensional compensation.

5. A method as recited in claim 4 wherein the component of the deviation along the optical path ($\Delta_z$) maintains the intended target position beyond a distance "d" from the volume of implant material.

6. A method as recited in claim 1 further comprising the step of accounting for the wavelength ($\lambda$) of the laser beam in the calculating step.

7. A method as recited in claim 1 wherein the laser beam is a pulsed laser beam.

8. A method as recited in claim 7 wherein each pulse in the laser beam has a pulse duration less than one nanosecond.

9. A method as recited in claim 1 wherein the volume of implant material is selected from a group comprising a multifocal Intraocular Lens (IOL), a customized lens, a customized inlay, a corneal lens and a corneal inlay.

10. A method for directing the focal point of a laser beam along an optical path through an implant material to an intended target position outside the implant material which comprises the steps of:
    using a reference datum to identify the intended target position for the focal point;
    calculating a refracted target position of the focal point, said refracted target position accounting for refractive optical characteristics introduced by the implant material on the optical path;
    measuring a deviation between the intended target position and the refracted target position;
    adding the deviation to the refracted target position to coincide the refracted target position with the intended target position; and
    focusing the laser beam to the focal point after the adding step.

11. A method as recited in claim 10 wherein a volume of implant material is positioned on the optical path for purposes of the calculating step and wherein the volume of the implant material is defined to include dimensional measurements of the volume, a refractive index of the implant material, and a configuration of the volume.

12. A method as recited in claim 11 wherein the reference datum is selected from a group comprising Optical Coherence Tomography (OCT), Scheimpflug imaging, confocal imaging, optical range finding, two-photon imaging or acoustical (non-optical) imaging techniques.

13. A method as recited in claim 11 wherein the reference datum is an algorithm.

14. A method as recited in claim 11 wherein the deviation ($\Delta_{xyz}$) provides for a three dimensional compensation, and wherein the component of the deviation along the optical path ($\Delta_z$) maintains the intended target position beyond a distance "d" from the volume of implant material.

15. A method as recited in claim 11 further comprising the step of accounting for the wavelength ($\lambda$) of the laser beam in the calculating step.

16. A method as recited in claim 11 wherein the laser beam is a pulsed laser beam, and wherein each pulse in the laser beam has a pulse duration less than one nanosecond.

17. A method as recited in claim 11 wherein the volume of implant material is selected from a group comprising a multifocal Intraocular Lens (IOL), a customized lens, a customized inlay, a corneal lens and a corneal inlay.

18. A computer program product for use with a computer to direct the focal point of a laser beam along an optical path through an implant material to an intended target position outside the implant material, wherein the computer program product comprises program sections for, respectively:
    using a reference datum to identify the intended target position for the focal point;
    calculating a refracted target position of the focal point, said refracted target position accounting for refractive optical characteristics introduced by the implant material on the optical path wherein the optical path of the laser beam is directed relative to the implant material and the implant material is defined to include dimensional measurements, a refractive index of the implant material, and a configuration of the implant material;
    measuring a deviation between the intended target position and the refracted target position; and
    adding the deviation to the refracted target position to coincide the refracted target position with the intended target position.

19. A computer program product as recited in claim 18 wherein the reference datum is established using Optical Coherence Tomography (OCT) techniques and wherein the deviation ($\Delta_{xyz}$) provides for a three dimensional compensation, and wherein the component of the deviation along the optical path ($\Delta_z$) maintains the intended target position beyond a distance "d" from the volume of implant material.

* * * * *